United States Patent
Chatard (10) Patent No.: US 6,658,919 B2
(45) Date of Patent: Dec. 9, 2003

(54) METHOD FOR MEASURING GAS PERMEABILITY OF A COATING ON A PLASTIC WALL AND DEVICE FOR IMPLEMENTING THE METHOD

(75) Inventor: Dominique Chatard, Heidelberg (DE)

(73) Assignee: Tetra Laval Holdings & Finance S.A., Pully (CH)

(*) Notice: Subject to any disclaimer, the term of this patent is extended or adjusted under 35 U.S.C. 154(b) by 0 days.

(21) Appl. No.: 10/221,460

(22) PCT Filed: Mar. 14, 2001

(86) PCT No.: PCT/EP01/02842

§ 371 (c)(1),
(2), (4) Date: Sep. 11, 2002

(87) PCT Pub. No.: WO01/69201

PCT Pub. Date: Sep. 20, 2001

(65) Prior Publication Data

US 2003/0046982 A1 Mar. 13, 2003

(30) Foreign Application Priority Data

Mar. 15, 2000 (DE) .......................... 100 12 446

(51) Int. Cl.[7] .............................................. G01N 15/08
(52) U.S. Cl. ........................................................ 73/38
(58) Field of Search ............................................. 73/38

(56) References Cited

U.S. PATENT DOCUMENTS 4,660,411 A * 4/1987 Reid
4,858,767 A * 8/1989 Myers et al.
5,591,898 A    1/1997 Mayer ............................ 73/38
6,009,743 A    1/2000 Mayer ............................ 73/38

FOREIGN PATENT DOCUMENTS

| DE | 39 33 382 C2 | * | 10/1989 |
| DE | 42 25 984 A1 | * | 8/1992 |
| EP | 0 764 479 A1 | * | 3/1997 |
| EP | 0 305 660 A2 | * | 6/1998 |

* cited by examiner

Primary Examiner—Hezron Williams
Assistant Examiner—Jay L Politzer
(74) Attorney, Agent, or Firm—Paul & Paul (57) ABSTRACT

Described is a method of measuring the permeability of a coating (3) on a plastic wall (1) to low-molecular gases, wherein the diffusion coefficient and/or solubility coefficient of the coating (3) with respect to the low-molecular gases is an order of magnitude lower than that of the plastic wall (1), wherein the space (4) on the coating side is subjected to the action of a first fluid (5) and is flushed through therewith until only said first fluid (5) is in the space. Also described is a device for carrying out the method. To measure the barrier property of the coating (3) it is provided that the first fluid includes a test medium (5), a component which can diffuse into the plastic wall (1) and be absorbed there, after the space (4) is flushed the test medium (5) is removed therefrom, thereafter the coated space (4) is subjected to the action of an extraction medium (7) in which the component is well soluble and can be measured, and the concentration of the component in the extraction medium (7) is measured.

8 Claims, 5 Drawing Sheets

METHOD FOR MEASURING GAS PERMEABILITY OF A COATING ON A PLASTIC WALL AND DEVICE FOR IMPLEMENTING THE METHOD

The invention concerns a method of measuring the permeability of a coating on a plastic wall to low-molecular gases, for example oxygen, wherein the diffusion coefficient and/or solubility coefficient of the coating with respect to the low-molecular gas is approximately an order of magnitude lower than that of the plastic wall, in which the space on the coating side is subjected to the action of a first fluid and is flushed through until substantially only said first fluid is in said space.

It is known for fluid packs to be made from plastic material, for example in the form of bottles with an opening at the top. Such bottles are produced from polyethylene terephthalate (PET) and are used in many cases for packaging for example water. It is known that the walls of the plastic packs are permeable in relation to low-molecular gases, and for that reason the periods of time for which it is possible to keep liquid foodstuffs, in particular juices and $CO_2$-containing mixed drinks, are limited. In order to prevent the oxygen which is responsible for this from entering the pack or the carbon dioxide from escaping and in order in that way to make it possible to make better use of such plastic packs for liquid foodstuffs, manufacturers have occasionally gone over to coating the inside or the outside of the walls of those plastic packs. An example of such a known coating process for improving that so-called barrier property of plastic packs is plasma-enhanced coating from the gaseous phase (the English abbreviation used is PECVD). In that respect, in the case of the inner coating, a gas mixture is introduced into the pack or the hollow body. Electromagnetic energy is radiated thereinto, and fires the plasma, and in that treatment procedure, for example a vitreous silicon oxide or an amorphous carbon layer is applied in the interior of the hollow body. Low-molecular gas, for example oxygen or carbon dioxide, by virtue of that additional barrier, can penetrate through the plastic walls substantially less to not at all, and low-molecular organic compounds can also no longer penetrate into the plastic material, with the consequence that, in the case of packaged liquid foodstuffs, the drinks can thereby keep their taste and their quality for substantially longer. There are however various factors which involve a coating of different thicknesses on the wall surface, for example the differing configuration of the coated bodies.

In accordance with another known method, X-ray fluorescence is used to measure on a wall portion which is cut out of the bottle, whether an application has taken place. This method also suffers from the disadvantage that it is not possible to establish whether the application is homogenously distributed on the surface and the coating therefore enjoys a good barrier property. In addition this elementary analysis can only be established on a stamped-out portion of the wall of the pack.

Therefore a further method has been developed whereby the barrier property of a coating on a plastic wall is measured by means of the oxygen which diffuses through the wall and the coating. For example a pack which is in air is flushed in the interior with nitrogen for a period of one day until the interior of the pack is certain to contain almost no longer any oxygen, while outside the pack there is a gas with 21% oxygen. If, after that flushing operation with nitrogen, the internal atmosphere of the hermetically sealed pack is left at rest, then the oxygen which possibly accumulates there in the course of time originates from the atmosphere surrounding the pack. That oxygen has then migrated from the outside through the plastic wall inwardly. After a waiting time of at best about twenty-four hours (typically up to three weeks), this measuring method provides that a steady final value in respect of the oxygen content in the atmosphere in the interior of the pack has become established. If that value is compared to a predetermined barrier value, it is then possible to establish whether the measured pack has been coated with a sufficiently good barrier. There is the disadvantage here that this known checking method requires a very long period of time so that the method can scarcely be used in the course of pack production as real time measurement is practically impossible to implement.

Therefore the object of the invention is to provide a method of the kind set forth in the opening part of this specification, by means of which the barrier property of the coating can be measured in a relatively short time, reliably and possibly for the entire surface of the coating, without destroying the body or the pack having the plastic wall.

In accordance with the invention that object is attained in that:

firstly the plastic wall is subjected to the action of a fluid which contains a test medium with at least one component which can diffuse into the plastic wall and be absorbed there, after the step of subjecting the coated space to the action of the fluid test medium deposited on the coated surface is removed therefrom, thereafter the coated space is subjected to the action of an extraction medium in which the test medium is well soluble and the test medium can be measured, and the concentration of the test medium in the extraction medium is measured.

This novel measuring method can provide for measuring the coating of the entire surface of a plastic wall, for example on the inside or the outside of a pack, which for example can be in bottle form, in regard to the barrier properties. It is therefore possible to measure whether low-molecular gases, preferably oxygen or carbon dioxide, can or cannot diffuse through the coating. If the coating is non-homogenous or if there are indeed places at which the wall of the pack is not coated at all, a markedly greater degree of diffusion of oxygen will be measured than if the coating is homogenous on the entire surface area in such a way that the oxygen cannot pass through the wall, without overcoming the barrier.

Both in the known method and also in the method according to the invention the space on the coating side, in the case of an internal coating therefore the internal space of the pack, is admittedly subjected to the action of a first fluid, for example flushed therewith, and is then flushed through until there is no longer any low-molecular gas in that space, which is intended to be prevented by the coating from passing through or diffusing through the plastic wall. In the known case the coated space is subjected to the action of nitrogen which is not a test medium. In accordance with the invention in contrast the first fluid contains a test medium for example acetaldehyde or hydrogen peroxide ($H_2O_2$). In the known method the flow of the low-molecular gas, for example oxygen, is always measured in one direction. For example the method involves measuring whether oxygen outside the plastic pack (in the air) diffuses through the plastic wall into the interior thereof, in spite of the coating. A reversed flow is neither produced nor measured. In accordance with the invention in contrast the coated space is admittedly also flushed with the first fluid containing the test medium, for example $H_2O_2$, but no account whatsoever is taken of the oxygen outside the pack. Rather, such a test medium is selected, which can diffuse into the plastic wall and also be absorbed there. If the coating were theoretically very good with a 100% barrier property, then no test medium would be absorbed in the coating and definitely not in the plastic wall, it could thereafter also not be extracted and consequently it could not be measured. The gas flow is therefore provided in two directions, more specifically for example from the interior of the pack in the plastic walls outwardly and thereafter back again out of those walls or the coating back into the internal space in the pack. The advantageous independence of low-molecular gases which are outside the pack is recognised, insofar as the internal space is coated (and vice-versa). It would in that respect moreover be possible to introduce a plurality of various test media into the first fluid.

Destruction of the plastic wall is avoided. There is no need for wall portions to be stamped out and measured separately. In spite of measurement of the entire hollow body the barrier property is checked in a relatively short period of time. Good reliable measurements have already been obtained in ten minutes or less. Measuring apparatuses for measuring the concentration of one medium in another are available in the art. It is possible to accurately and rapidly measure how much test medium, for example $H_2O_2$, is contained in an extraction medium, for example water or air.

Under other conditions it is possible for the total measurement procedure to be carried out within two hours, in which respect it has been found that this period of time is always still reasonable and useable for production monitoring. More specifically, in that way it is possible to increase in particular the level of measuring accuracy as the total amount of test medium extracted increases with an increasing extraction time.

The basic notion of the novel measuring method is that the attempt is made to introduce a well-chosen test medium from the coating side into the coating and/or the plastic wall therebehind (subjecting it to the action thereof) so that at least one diffusible and absorbable component can accumulate in the plastic wall and/or its coating, whereupon any test medium which has been deposited is removed again by means of a propellant, for example gas or liquid, from the surface at the coating side. Then, after that process of diffusing into the material, the test medium will try to diffuse out of same again. In accordance with the invention in the meantime the coated space is subjected to the action of an extraction medium, for example water or air. This must be matched to the test medium so that the test medium can dissolve in the extraction medium and can also be measured in the extraction medium. The test medium therefore issues from the plastic wall and the coating into the extraction medium and there affords a level of concentration which in accordance with a calibration curve permits information to be provided about the quality of the barrier property of the coating.

It is to be noted that preferably a 25% aqueous solution of $H_2O_2$ is used as the test medium for coated PET containers.

It is desirable in accordance with the invention if, prior to subjecting the coated space to the action of the first fluid, said space and the surface of the coating are heated in a conditioning phase to a temperature at which the material of the coated plastic wall does not deform. In the case of PET as the plastic material it is desirable to effect heating to less than 60° C. In that respect it is advantageously sufficient if an internally coated pack is heated only on the inside by blowing with a suitably warmed air flow. That conditioning procedure expedites the measuring method because thereafter the test medium diffuses more quickly into the layers to be investigated.

For further expedition of the entire measuring method it is desirable if, in accordance with the invention, the operation of removing the test medium from the coated surface is effected by blowing on it with warm air. While that step of removing the test medium for typical PET bottles of a volume of about 0.5 is deemed to be sufficiently concluded in just 20 seconds, that blowing operation and thus the operation of removing the test medium can be prolonged by between 1 and 2 minutes if the test medium is partially deposited by condensation on the surface of the coating. The tendency to experience condensation can depend on the concentration of the relevant component of the test medium, for example the concentration of hydrogen peroxide in water. Blowing on the coated surface with warm air at any event makes it possible to remove all residual amounts of test medium from the surfaces which are acted upon. A further advantageous expedition in the measuring method and ensuring reliable results is achieved if in accordance with the invention the extraction medium is at a temperature of about 20° C. The extraction time can even be further curtailed to a few seconds if the temperature of the extraction medium is increased to non-critical values of for example between 50° C. and 60° C. (non-critical in the sense of successful measurement without interference factors).

A further advantageous configuration of the invention provides that the test medium is an approximately 25% aqueous solution of $H_2O_2$ and, for acting on the space at the coating side, that test medium is blown in, in a predetermined metered amount with warm air for between 2 and 10 seconds, preferably for between 3 and 7 seconds, and particularly preferably for 5 seconds.

It is also possible for the test medium used to be $CO_2$; while the extraction medium can be nitrogen or an inert gas, preferably helium or argon. The method according to the invention can also be carried into effect in relation to walls of polyethylene or PVC. The device for carrying out the above-described method has an intermittently movable conveyor, over which a plurality of treatment stations are arranged at a spacing one behind the other in the conveyor direction. In accordance with the invention packs which are open at one side are held with their opening upwardly on that conveyor and conveyed from one treatment station into the next. Then, in accordance with the invention, in each treatment station a fluid introduction inlet can be arranged above the opening of the pack and connected at the upstream side to a feed conduit. In the last treatment station moreover the opening of the pack can be sealingly connected to a fluid discharge conduit. The treatment can be considered to be conditioning, subjecting the pack to the action of the test medium (for example spraying in the aqueous $H_2O_2$ solution), drying, extracting and measuring. One or more treatment stations can be used for the individual treatments. Through the fluid introduction inlet, different gases and/or liquids can be introduced into the pack through the opening of the pack and possibly taken out of the pack. In addition in the last treatment station a fluid discharge conduit can be applied to the pack. In that way it is possible for the amount of previously introduced fluid, which is urged out or sucked out, to be removed from the pack in quantitatively measurable manner. By embracing the fluid introduction inlet, through which for example the test medium has been introduced centrally in the above-described manner, the fluid discharge conduit can provide that a desired metered amount of the previously introduced fluid, for example the extraction medium, is removed and fed to a measuring chamber.

A further configuration of the device according to the invention can provide that in each treatment station after the conditioning operation the opening of the pack can be sealingly connected to a fluid discharge conduit. If $CO_2$ is used as the test medium, this means that all packs to be measured are sealed off in relation to an outside atmosphere in which traces of gas are or can be present, which under some circumstances can result in falsification of the measurement result.

Specifically it is of particular advantage if in accordance with the invention the following treatment stations are provided in the direction of conveying movement of the conveyor:

1. a first treatment station for conditioning the pack with air,
2. a second treatment station for subjecting the pack to the action of test medium,
3. at least one third treatment station for removal from the pack of the test medium which has been deposited at the surface and which has not diffused into the wall,
4. a fourth treatment station for introducing extraction medium into the pack, and
5. a fifth treatment station for measuring the concentration of the test medium in the extraction medium.

In order to make the removal of residual amounts of test medium from the surface which has been acted upon more intensive, it may be appropriate to use three treatment stations instead of one. The entire measuring method can then be carried out expeditiously even under those conditions under which the test medium has been deposited forming a film of fluid on the surface due to condensation. The dry air which is blown in can then be used in each of the three treatment stations for removal of the test medium.

The component of the test medium which can diffuse into the material of the plastic wall or the coating is to be present in the highest possible level of concentration. The concentration gradient should be a maximum in relation to the other constituents of the medium so that a sufficient amount of that component of the test medium can be incorporated in the coated plastic wall. The measurement is proportionally more accurate, the greater the amount of test medium which first diffuses into the wall in a short unit of time and is thereafter extracted.

The test medium must also be so stable that it does not break up until the end of the operation of subjecting the coated surfaces to the action thereof. At least the above-mentioned component of the test medium should not break down. Those conditions are advantageously fulfilled when using the 25% aqueous $H_2O_2$ solution.

The test medium should also be heatable to the above-mentioned temperatures which are used in the measuring method. In other words, the test medium must enjoy good temperature resistance over the entire meaningful range of parameters of the measuring method.

The measuring method is generally monitored and governed by persons. The test medium should therefore not be harmful to the health of the operating personnel. It is preferable if an operator can carry out all steps in the method without protective clothing.

Packs are frequently used in the field of foodstuffs, so that the test medium should not be in any way toxic. It must be provided that the test medium is compatible with foodstuffs, without any risk.

If the test medium or at least the above-mentioned component thereof is introduced into the pack in the gaseous phase, homogenous distribution thereof over the entire surface of the coated pack is also guaranteed. All regions of a coating can then be jointly measured by a measuring procedure.

The test medium must also be of such a nature in chemical and physical terms that it does not destroy the coating.

Similar conditions are also to be provided for the extraction medium for which for example water or air or inert gases can be used.

The extraction medium should also be harmless in regard to foodstuffs and stable without the risk of decomposing, it should not destroy the coating and it should make it possible for the test medium to transfer readily into the extraction medium.

The steps mentioned in accordance with the invention set forth a measuring method in which the essential conditions can be monitored, that is to say checked, and can also be observed, and which delivers reliable results in 10 minutes or less.

For the device for carrying out the measuring method, in particular the amounts of air, temperature, time and also the amount of test medium and also extraction medium can be reliably checked and maintained.

Further advantages, features and possible uses of the present invention will be apparent from the description hereinafter of a preferred embodiment with reference to the accompanying drawings in which:

FIGS. 1 to 6a each diagrammatically show on the left a portion of a coated wall, besides which gas molecules are to be found on the right, wherein

Figure 5A:
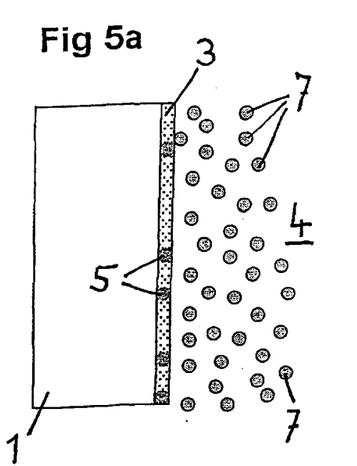
FIG. 5a shows the extraction phase in the case of a continuous coating.
Figure 5B:
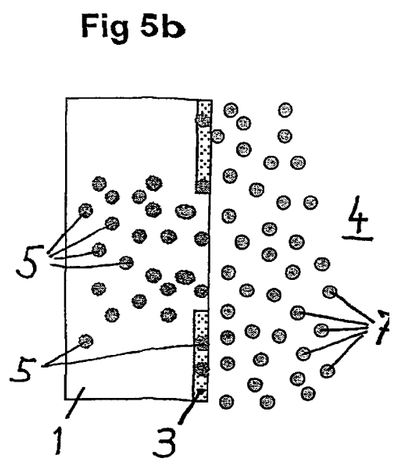
FIG. 5b shows the extraction phase in the case of an interrupted coating.
Figure 6A:
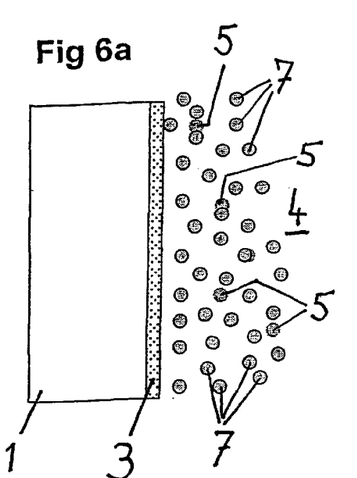
FIG. 6a shows the measuring phase in the case of a continuous coating.
Figure 7:
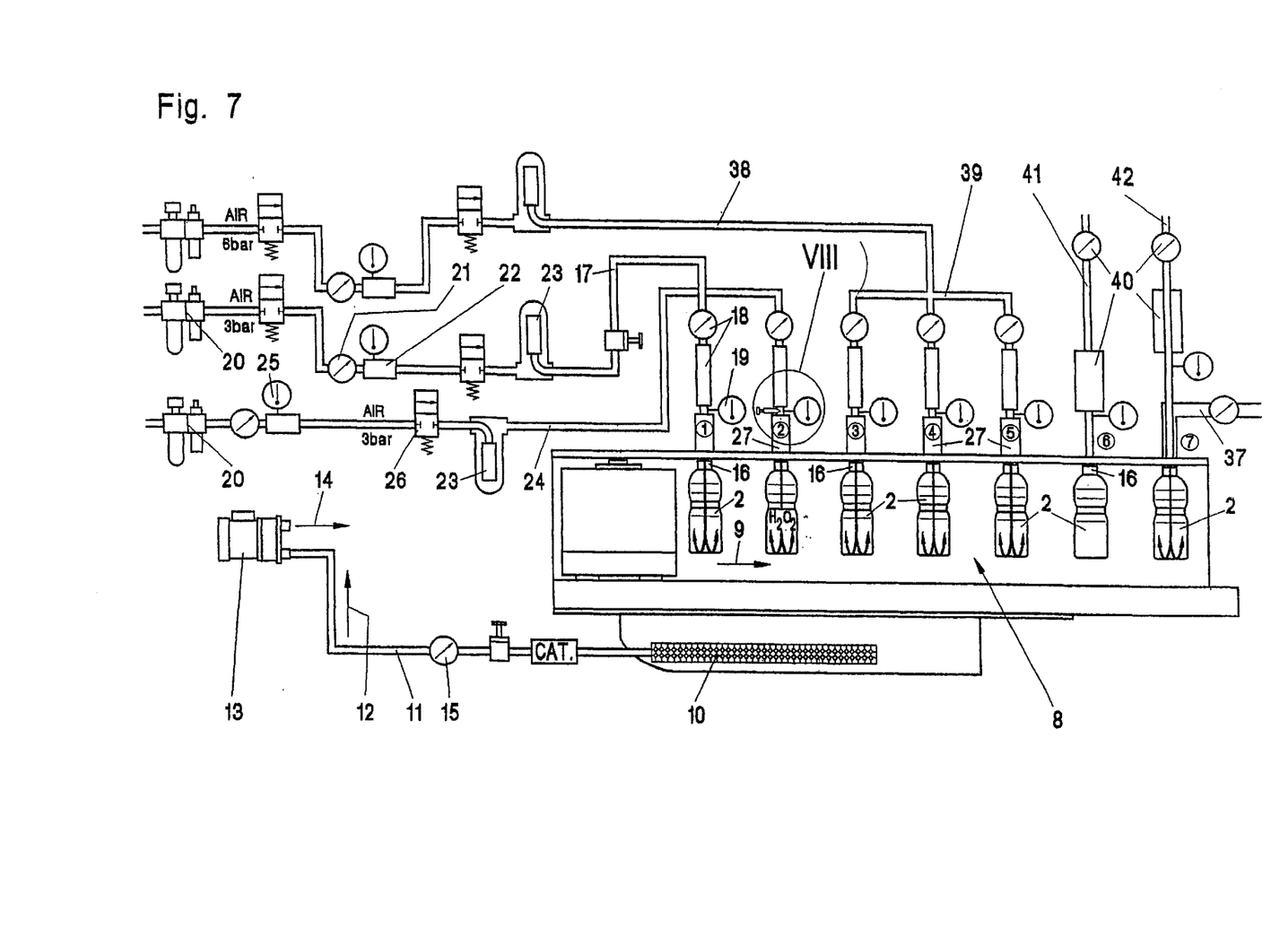
FIG. 7 is a diagrammatic and partly broken-away view showing the installation as a device for carrying out the measuring method.

FIGS. 1 to 6a each diagrammatically show on the left a portion of a plastic wall 1 of a fluid pack 2 in bottle form, as illustrated in FIG. 7, in which respect it is to be assumed that the outside of the pack is in each case to the left of the plastic wall 1. Towards the inside the pack is provided with a coating 3. The internal space 4 of the pack 2 is to the right of the outer surface of the coating 3 in each case. These illustrations also apply to the situation where reference numeral 4 denotes the external space and the space which is on the opposite side of the plastic wall 1 is the internal space.

The space 4 is then the space on the coating side. In the embodiment illustrated here the permeability of the coating 3 in relation to oxygen is to be measured, in which respect both the diffusion coefficient and also the solubility coefficient of the coating 3 is smaller by an order of magnitude than that of the plastic wall 1.

Added to the so-called first fluid is a test medium in the form of a 25% aqueous $H_2O_2$ solution. In that way the component contained in that solution, for example the $H_2O_2$ molecule, can diffuse into the plastic wall 1 and be absorbed there. For that purpose, as shown in FIG. 1, firstly the space 4 at the coating side is subjected to the action of the first fluid which contains the $H_2O_2$ vapour.

Figure 1:
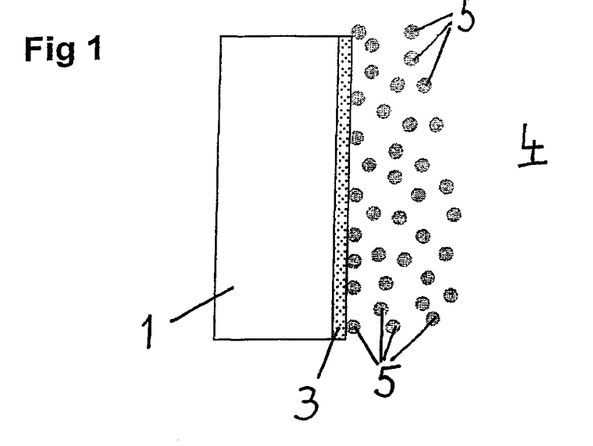
FIG. 1 shows the first phase in which $H_2O_2$ as the test medium is introduced into the space beside the coating.

The hydrogen peroxide molecules contained in the fluid can be deposited on the one hand at the outside surface of the coating 3, in which respect it is possible to talk of an adsorption phase which is diagrammatically shown in FIG. 1 by virtue of some $H_2O_2$ molecules 5 externally adhering to the coating 3, while the other $H_2O_2$ molecules move freely in the space 4. All circles shown in grey in the Figures represent the $H_2O_2$ molecules 5.

Optionally, before the space 4 is subjected to the action of the fluid, that space 4 can be heated to a temperature of about 55° C. by a flow of air which is blown in, in order on the one hand to speed up the diffusion processes and on the other hand not to excessively greatly heat the material of the plastic wall 1, for example PET, so that the pack overall cannot suffer deformation.

In the preferred embodiment here the $H_2O_2$ molecules are blow into the space 4, in conjunction with hot air, and the operation of subjecting the space to the action of the hydrogen peroxide molecules 5 lasts for five seconds. In this case a part of the hydrogen peroxide (of the 25% solution) can also condense on the surface of the coating 3.

Figure 2A:
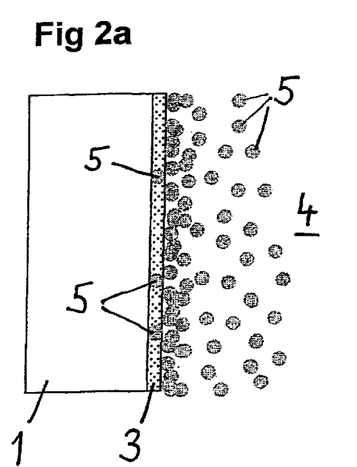
FIG. 2a shows the absorption phase with continuous coating.
Figure 2B:
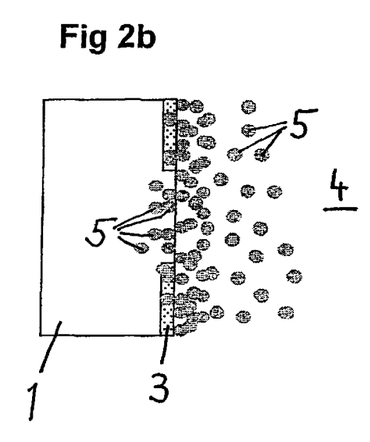
FIG. 2b shows the absorption phase in the case of an interrupted coating.

FIG. 2a shows how individual $H_2O_2$ molecules 5, in this absorption phase, even migrate into the coating 3 and are absorbed there. Three such molecules 5 are shown in the diagrammatic view in FIG. 2a. FIG. 2b shows the same absorption phase in the case of a poor, irregular or interrupted coating 3. It will be seen how a relatively large number of $H_2O_2$ molecules 5 diffuse into the plastic wall 1 at the place where the coating is interrupted (in FIG. 2b, approximately in the middle of the coating).

Figure 3A:
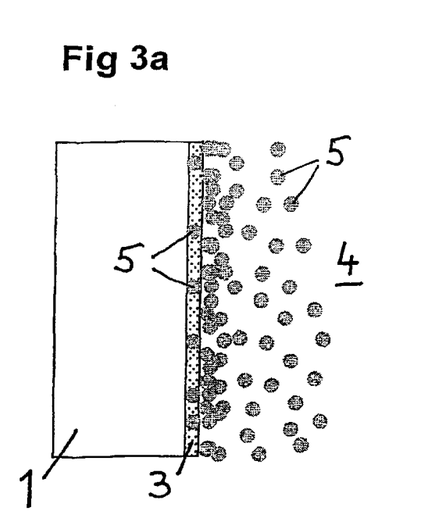
FIG. 3a shows the diffusion phase in which $H_2O_2$ begins to diffuse into the coating, in the case of a continuous coating, FIG. 3b also shows the diffusion phase, but here in the case of an interrupted coating.
Figure 3B:
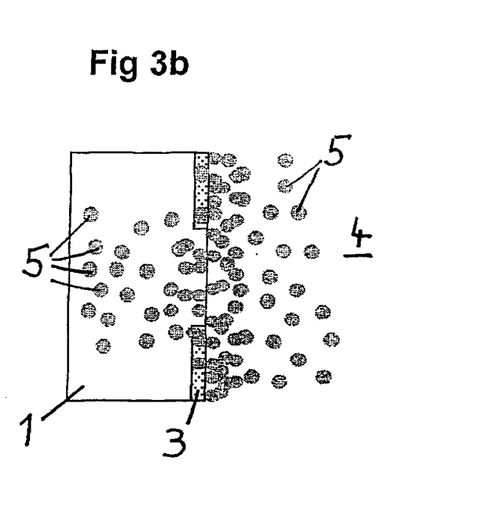

In the diffusion phase as shown in FIGS. 3a and 3b that diffusion into the good closed coating 3 as shown in FIG. 3a continues just as into the interrupted coating shown in FIG. 3b. In the latter case in this diffusion phase numerous $H_2O_2$ molecules 5 have penetrated in the plastic wall 1. The condensation film on the surface of the coating 3 is represented in FIGS. 3a and 3b by molecules 5 which bear against each other and lie against the surface of the coating 3.

After that diffusion phase, in accordance with the measuring method it is assumed that an amount of $H_2O_2$ molecules 5, which is sufficiently great for identification by a measuring procedure, has collected in the coating 3 and/or the plastic wall 1 (FIG. 3b), so that further diffusion is no longer necessary. The space 4 at the coating side can therefore be freed of the $H_2O_2$ (of the solution) of the test medium. Therefore the further step of removing the test medium from the surface of the coating 3 now takes place. That is effected by drying. If a thicker condensation film should have formed on the surface of the coating 3, removal of the residual amounts of hydrogen peroxide can also be achieved by flushing.

Figure 4A:
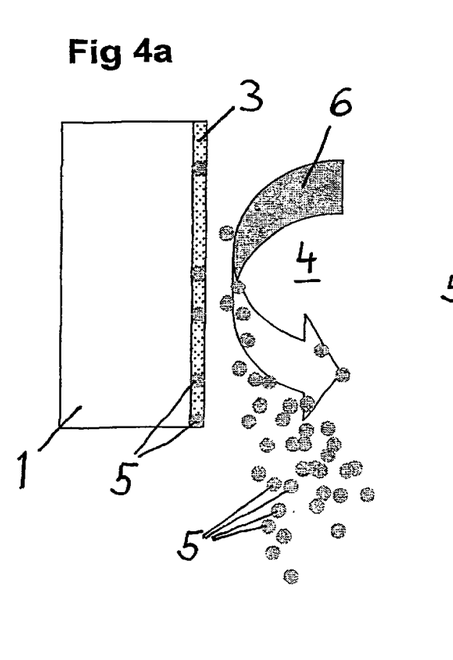
FIG. 4a shows the drying phase in the case of a continuous coating.

In FIG. 4 the arrow 6 denotes dry air which (possibly after previously being rinsed off with water) is blown into the space 4 at the coating side, in order to remove the whole of the residual amount from the space 4 and from the surface of the coating 3. It is possible to see in FIG. 4a in relation to the continuous coating 3 that the $H_2O_2$ molecules 5 in the space are entrained by the air flow 6 and are removed downwardly.

Figure 4B:
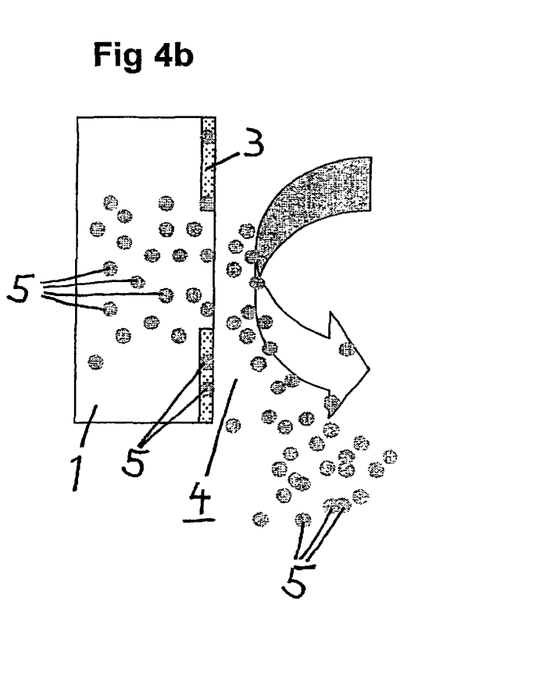
FIG. 4b shows the drying phase in the case of an interrupted coating.

It will be seen in relation to the interrupted coating 3 shown in FIG. 4b how the $H_2O_2$ molecules 5 are admittedly also entrained out of the space 4 by the air 6 and are removed downwardly, but also how, besides the molecules 5 which are retained in the coating 3, a rather large number of molecules 5 also remains in the plastic wall 1, because they cannot be engaged and removed by the air 6.

Thereafter the plastic wall 1 and the coating 3 thereof is approximately in the condition illustrated in FIGS. 5a (and 5b for the interrupted coating). The space 4 is firstly filled with hot air and now filled with water at 20° C. as an extraction medium. Those water molecules are represented in FIGS. 5a to 6b by black circles (in contrast to the light-grey circles which represent the $H_2O_2$). After the space 4 has been flushed with water (water molecules 7), the condition is then as shown in FIG. 5a for the continuous coating 3 and FIG. 5b for the interrupted coating.

Figure 6B:
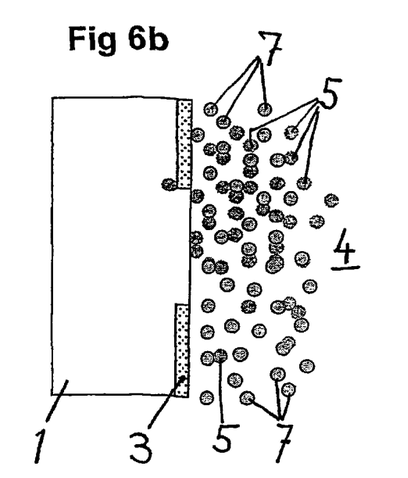
FIG. 6b shows the measuring phase in the case of an interrupted coating.

The $H_2O_2$ molecules contained in the plastic wall 1 and the coating 3 thereof now begin to be extracted. Those $H_2O_2$ molecules 5 (light grey) therefore begin to migrate towards the right out of the wall 1 with the coating 3 into the space 4. Depending on the respective embodiment involved that extraction phase can last from 5 minutes to 2 hours. Thereafter the condition shown in FIG. 6a for the continuous coating 3 and FIG. 6b for the interrupted coating 3 is reached. In that condition as shown in FIGS. 6a and 6b the actual measurement procedure can begin. It can be seen from FIGS. 6a and 6b that between the black circles representing the water molecules 7 there are light-grey circles which represent the $H_2O_2$ molecules. In the case of the "good", namely continuous coating 3 shown in FIG. 6a, only a few (in this example four) $H_2O_2$ molecules 5 are to be found among the water molecules 7. Therefore a low level of concentration of test medium in the space 4 will be measured, with the conclusion that the coating 3 has good barrier properties because only few $H_2O_2$ molecules (test medium) were able to penetrate into the coating and/or the plastic wall 1, which were thereafter extracted.

A condition as shown in FIG. 6b occurs in the case of the interrupted coating 3. The $H_2O_2$ molecules 5 which have migrated into the plastic wall 1 in FIG. 5b have admittedly migrated towards the right into the space 4 through the opening in the coating 3 (have been extracted), but it is possible to see a much greater number of $H_2O_2$ molecules 5 among the water molecules 7 in FIG. 6b than in FIG. 6a. The operator can therefore measure a high concentration of $H_2O_2$ (test medium) in the water (extraction medium), with the conclusion that the coating 3 is not good, more specifically it is interrupted.

Figure 8:
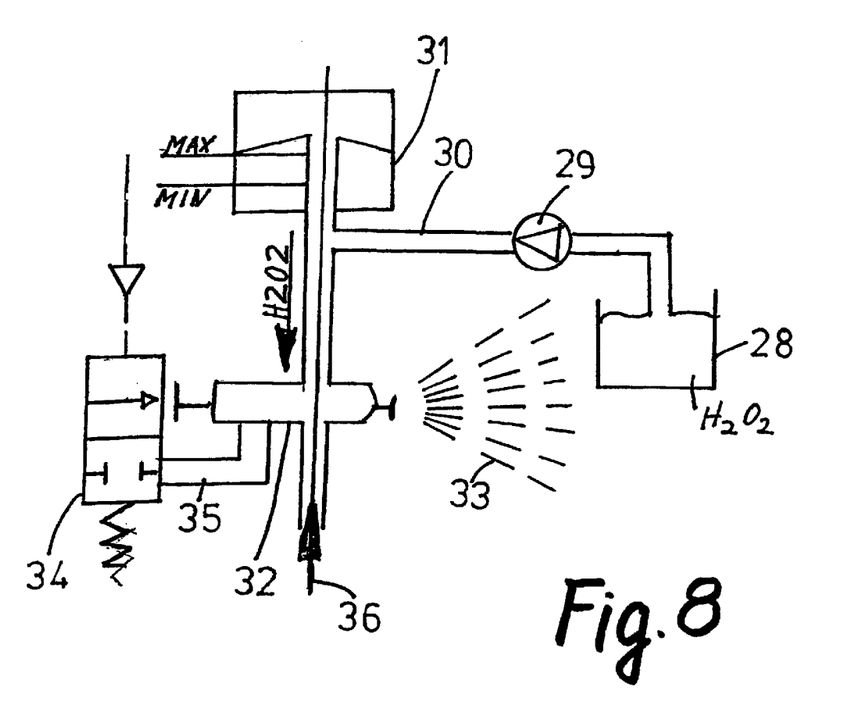
FIG. 8 is a view on an enlarged scale showing the detail indicated at VIII in FIG. 7.

These method steps which are shown in principle in FIGS. 1 to 6b can be carried out in the device illustrated in FIGS. 7 and 8.

In FIG. 7, in a transport space which is generally identified by reference 8, the conveyor direction 9 is illustrated by an arrow which points from left to right in FIG. 7. A per se known conveyor can be considered here, which moves the packs intermittently from left to right at predetermined spacings. Disposed under the transport space is a catalyst 10 which cleans the exhaust air which is sucked through the conduit 11 in the direction of the exhaust air arrow 12 to the pump 13 and is expelled therefrom in the direction of the arrow 14. The exhaust air which flows through the conduit 11 can also be measured in respect of its amount by means of the flowmeter 15.

Seven treatment stations [1] to [7] are arranged above the transport space 8 which can also be in the form of a hygiene space in which therefore the germ loading in the atmosphere is reduced. The packs 2 which are open at one side and which are in bottle form have a respective opening 16 facing upwardly and are held on the conveyor (conveyor direction 9) in such a way that in each of the treatment stations [1] to [7] a fluid introduction inlet (not shown) can be arranged above the opening 16 of the pack. At the upstream end each fluid introduction inlet is connected to a feed conduit.

For the treatment station 1 this involves the feed conduit 17 through which is fed dry air whose amount is measured by way of a flowmeter 18 and whose temperature is measured by way of a thermometer 19. The treatment station [1] here involves the conditioning operation. The dry air flows by way of an oil separator 20 through a valve, a flowmeter 21, a heat exchanger 22 and by way of a filter 23 to the treatment station [1] (for the conditioning phase).

In the treatment station [2] dry air is also pumped at a temperature of about 100° C. through the feed conduit 24. Disposed therein is the oil separator 20, the temperature measuring device 25, the pressure regulating valve 26, the filter 23 and so forth. At the location of the detail indicated at VIII in FIG. 7 in the embodiment illustrated here, a 25% aqueous solution of hydrogen peroxide ($H_2O_2$) as the test medium is sprayed in, as can be seen in FIG. 8. The spraying operation is effected into the feed conduit 24 at the location above the heat exchanger 27. In FIG. 8 the storage vessel for $H_2O_2$ is identified by reference 28, from which the aqueous solution is pumped by means of the pump 29 and by way of the conduit 30 into the feed container 31 until the level of liquid is between the markings MAX and MIN. In this embodiment the metered amount of the 25% aqueous solution of $H_2O_2$ is 200 $\mu l$. That comparatively small dosage is sprayed by way of the nozzle 32 into the feed conduit 24 (not shown in FIG. 8), as indicated by the spray jets 33. A pneumatic valve 34 provides that a mixture of (possibly sterile) air and $H_2O_2$ is produced in the nozzle 32 and then sprayed, as indicated by the spray jets 33. The $H_2O_2$ is fed in FIG. 8 from above from the feed container 31, in accordance with the amount controlled by way of the pressure conduit 35 in the nozzle 32, and mixed with the sterile air which is introduced from below as indicated by the arrow 36. The spray jets 33 contain that sprayed mixture which is mixed with the dry air supplied through the conduit 24. By virtue of the arrangement of the opening 16 of the pack 2 under the outlet end of the feed conduit 24 that gas/$H_2O_2$ mixture passes into the bottle-shaped pack 2, there passes onto the bottom thereof and at the side upwardly through the opening 16 out of same again.

If $CO_2$ is used as the test medium instead of $H_2O_2$ (in another embodiment which is not shown), the opening 16 of the pack should be sealingly connected to a fluid discharge conduit in each treatment station from the treatment station [2] to the end as far as the treatment station [7], as is denoted in respect of the treatment station [7] at 37 and shown for all embodiments. The purpose of that sealing connection is that, when using $CO_2$ as the test medium, the measuring results should not be falsified by the proportion of $CO_2$ in the air.

The phase for removal of the test medium, in the illustrated embodiment the $H_2O_2$, is executed in the treatment stations [3] to [5]. In these drying phases also dry air is fed through the feed conduit 38 by way of the distributor 39 to the respective heat exchanger 27 and then downwardly to the pack 2. It is assumed that, after the interior of the pack has been flushed three times with the dry air, by way of the respective feed conduit 38, the test medium is reliably removed.

In the treatment station [6] pure water is fed to the pack 2 by way of the flowmeter 40, through the feed conduit 41. This involves the extraction medium into which the $H_2O_2$ molecules migrate. The extraction operation is effected in a few minutes, preferably in a period of between 1 and 9 minutes and particularly preferably and reliably in accordance with a test in 5 minutes.

In treatment station [7] $H_2O_2$-free gas, for example air, is fed to the interior of the pack 2 by way of the feed conduit 42 in order to expel the water partially charged with $H_2O_2$, as the extraction medium, through the fluid discharge conduit 37. Therein measurement of the $H_2O_2$ content is then effected within a period of 1 minute. The result obtained in that case is reliable and secure. The total time for carrying out the measuring method is less than 10 minutes if it is assumed that the extraction time is about 5 minutes.

The duration for removal of the test medium, for each treatment station, is set at 7 seconds. In the treatment stations [3] to [5] the $H_2O_2$ is therefore removed in 3×7 seconds, that is to say a total of 21 seconds.

Alternatively it is also possible to provide as the test medium $CO_2$ which can be very easily detected, for example optically.

In the foregoing description PET was assumed to be the material for the plastic wall 1. Other materials in relation to which the novel measuring method according to the invention can also be carried out are polyethylene, PVC and aliphatic polyamide which is also commercially available under the protected trade mark "Nylon". In regard to the chemical definition thereof attention is directed to Römpps Chemie-Lexikon (Römpps Chemical Dictionary), 8th edition, 1985, Volume 4.

Water and air were specified hereinbefore for the extraction medium, but it is also possible to use nitrogen or an inert gas such as preferably helium or argon.

List of References
1 plastic wall
2 liquid pack
3 coating
4 space on the coating side
5 $H_2O_2$ molecules
6 dry air (arrow)
7 water molecules introducing sterile air)
8 transport space
9 conveyor direction
10 catalyst
11 conduit
12 exhaust air
13 pump
14 arrow (exhaust air expulsion direction)
15 flowmeter
16 upper opening of the pack
17 feed conduit (dry air)
18 flowmeter
19 thermometer
20 oil separator
21 flowmeter
22 heat exchanger
23 filter
24 feed conduit
25 temperature measuring device
26 pressure regulating valve
27 heat exchanger
28 storage vessel for $H_2O_2$ 29 pump
30 conduit
31 aqueous solution
32 nozzle
33 spray jets
34 pneumatic valve
35 pressure conduit
36 arrow (direction of introducing sterile air)
37 fluid discharge conduit
38 feed conduit
39 distributor
40 flowmeter
41 feed conduit for water
42 feed conduit

What is claimed is:

1. A method of measuring the permeability of a coating on a plastic wall (1) to low-molecular gases, for example oxygen, wherein the diffusion coefficient and/or solubility coefficient of the coating with respect to the low-molecular gas is approximately an order of magnitude lower than that of the plastic wall (1), in which the space (4) only on the coating side is subjected to the action of a first fluid (5) and is flushed through until substantially only said first fluid (5) is in said space (4), characterised in that the first fluid is a test medium (5) with at least one component which can diffuse into the plastic wall (1) and be absorbed there, after the step of subjecting the coated space (4) to the action of the fluid test medium deposited on the coated surface is removed therefrom, thereafter the coated space (4) is subjected to the action of an extraction medium (7) in which the test medium (5) is well soluble and the test medium (5) can be measured, and the concentration of the test medium (5) in the extraction medium (7) is measured.

2. A method according to claim 1 characterised in that in the space (4) on the coating side said space and the surface of the coating are heated in a conditioning phase to a temperature at which the material of the coated plastic wall (1) does not deform.

3. A method according to claim 1 or claim 2 characterised in that the operation of removing the test medium (5) from the coated surface is effected by blowing on hot air.

4. A method according to one of claims 1 to 2 characterized in that the extraction medium (7) is at a temperature of about 20° C.

5. A method according to one of claims 1 to 2 characterized in that the text medium (5) is an approximately 25% aqueous solution of hydrogen peroxide and for the operation of acting on the space (4) on the coating side is blown thereinto in a predetermined metered amount with hot air for between 2 and 10 seconds, preferably between 3 and 7 seconds and particularly preferably for 5 seconds.

6. A device for carrying out the method according to one of claims 1 to 2 comprising an intermittently movable conveyor, over which a plurality of treatment stations are arranged one after the other in the conveyor direction (9), characterized in that each package (2) which is open at one side is held on the conveyor with its opening (16) upwardly, in each treatment station a fluid introduction inlet can be arranged above the each package opening (16) and is connected on the upstream side to a feed conduit (17, 24, 38, 41, 42), and in the last treatment station each package opening (16) can be sealingly connected to a fluid discharge conduit (37).

7. A device according to claim 6 characterised in that in each treatment station after the conditioning operation the package opening (16) can be sealingly connected to a fluid discharge conduit (37).

8. A device according to claim 6 characterized in that the following treatment stations are provided in the conveyor direction (9) of the conveyor:

a first treatment station for conditioning of the package (2) with air, a second treatment station for subjecting the package (2) to the action of test medium (5), at least one third treatment station for removal from the package (2) of the test medium (5) which is deposited at the surface and which has not diffused into the wall, a fourth treatment station for the introduction of extraction medium (7) into the package (2), and a fifth treatment station for measuring the concentration of a test medium (5) in the extraction medium (7).

* * * * *